(12) United States Patent
Fink et al.

(10) Patent No.: US 7,332,479 B2
(45) Date of Patent: Feb. 19, 2008

(54) EXTRACELLULAR NAD$^+$ AND CADPR AS POTENT ANTI-INFLAMMATORY AGENTS

(75) Inventors: Mitchell P. Fink, Pittsburgh, PA (US); Russell L. Delude, Pittsburgh, PA (US); Xianonan Han, Pittsburgh, PA (US)

(73) Assignee: University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 34 days.

(21) Appl. No.: 10/659,063

(22) Filed: Sep. 10, 2003

(65) Prior Publication Data

US 2005/0065109 A1    Mar. 24, 2005

(51) Int. Cl.
*A61K 31/70* (2006.01)
*A61K 31/7076* (2006.01)
*C07H 19/167* (2006.01)

(52) U.S. Cl. .......................... 514/46; 514/47; 514/886; 514/921; 536/26.1

(58) Field of Classification Search ................. 514/46, 514/47, 886, 921; 536/26.4
See application file for complete search history.

(56) References Cited

U.S. PATENT DOCUMENTS

| | | | | |
|---|---|---|---|---|
| 6,028,111 A | * | 2/2000 | Pero et al. ................. | 514/620 |
| 2002/0127646 A1 | * | 9/2002 | Lund et al. ................ | 435/69.1 |

OTHER PUBLICATIONS

Neurath et al. (Immunobiology, (Dec. 1997) 198 (1-3) 91-8) (Abstract Sent).*

* cited by examiner

*Primary Examiner*—Shaojia Anna Jiang
*Assistant Examiner*—Michael C. Henry
(74) *Attorney, Agent, or Firm*—Weingarten, Schurgin, Gagnebin & Lebovici LLP (57) ABSTRACT

A method of prophylaxis or treatment of inflammatory conditions, including, but not limited to, intestinal epithelial inflammation due to intestine-specific conditions (e.g., Crohn's disease or ulcerative colitis) or systemic causes of inflammation (e.g., endotoxemia, sepsis, hemorrhagic shock/resuscitation or pancreatitis) is disclosed. In the method of the invention, an affected patient is administered a therapeutically effective amount of a composition including an NAD-related compound, in a form that is accessible to a receptor molecule, conveyed in a pharmaceutically acceptable carrier vehicle. NAD-related compounds include nicotinamide adenine dinucleotide (NAD$^+$), cyclic adenosine diphosphate ribose (cADPR), or functionally equivalent analogues, derivatives, metabolites or agonists thereof or prodrugs therefor.

Also disclosed are ex vivo and in vivo assay methods to test candidate compounds for activity, kits for carrying out the therapeutic methods or the assay methods of the invention and articles of manufacture that include compositions for use in the methods of the invention and instructions for the use thereof.

6 Claims, 8 Drawing Sheets
(1 of 8 Drawing Sheet(s) Filed in Color)

EXTRACELLULAR NAD+ AND CADPR AS POTENT ANTI-INFLAMMATORY AGENTS

STATEMENT REGARDING FEDERALLY SPONSORED RESEARCH OR DEVELOPMENT

Part of the work leading to this invention was carried out with United States Government support provided under a grant from the National Institutes of Health, Grant Nos. R01-GM37631 and R01-GM58484. Therefore, the U.S. Government has certain rights in this invention.

CROSS REFERENCE TO RELATED APPLICATIONS

N/A

BACKGROUND OF THE INVENTION

A necessary function of the intestinal epithelium is the establishment of a selective barrier to allow the absorption of nutrients while restricting the uptake of toxic substances and microbes from the gut lumen. A major component of this epithelial barrier is the tight junction (TJ), a circumferential protein complex located at the apical/basolateral junction of opposing cells. The TJ complex is believed to be the point of cell-cell contact that presents the major barrier to paracellular transport[5,6].

Intestinal epithelial barrier function is compromised in a variety of inflammatory conditions including inflammatory bowel disease, cholestasis, hemorrhagic shock, and sepsis[7]. Many mechanisms, including activation of myosin light chain kinase and excessive nitric oxide (NO.) synthesis, have been proposed to explain the increase in paracellular permeability of intestinal epithelia following exposure to an inflammatory environment[8,9]. However, effective treatments are not available. Therefore, it would be advantageous to discover new pharmacological agents that are effective in preventing or treating a broad variety of inflammatory conditions, including compromised barrier function.

BRIEF SUMMARY OF THE INVENTION

Such agents are now available according to the present invention, which is directed to a method of prophylaxis or treatment of inflammatory conditions, including, but not limited to, intestinal epithelial inflammation due to intestine-specific conditions (e.g., Crohn's disease or ulcerative colitis) or systemic causes of inflammation (e.g., endotoxemia, sepsis, acute respiratory distress syndrome, rheumatoid arthritis, hemorrhagic shock/resuscitation or pancreatitis). In the method of the invention, an affected patient is administered a therapeutically effective amount of a composition including an NAD-related compound, in a form that is accessible to a receptor molecule, conveyed in a pharmaceutically acceptable carrier vehicle. An exemplary receptor molecule is CD38. NAD-related compounds include nicotinamide adenine dinucleotide (NAD+), cyclic adenosine diphosphate ribose (cADPR), or functionally equivalent analogues, derivatives, metabolites or agonists thereof or prodrugs therefor. Exemplary analogues include phosphorothioate analogues, N3'→P5' phosphoroamidate analogues and analogues with conformationally locked sugar rings.

In another aspect, to determine the suitability of specific NAD-related compounds for patient treatment, the present invention includes ex vivo and in vivo assay methods to test such candidate compounds for activity. Specific assay methods include testing a candidate compound for the ability to inhibit nitric oxide (NO.) production in an ex vivo inflammation model, e.g., using lipopolysaccharide (LPS)-stimulated RAW 264.7 murine macrophage-like cells or Caco-2 human enterocyte-like cells, as described herein; testing the candidate for the ability to inhibit hyperpermeability, e.g., in cytokine-stimulated Caco-2 cells, by measuring for an indication of normal expression and localization of tight junction proteins such as ZO-1 and occludin; and testing a candidate agent, e.g., for the ability to ameliorate LPS-induced mortality in a mouse model.

Kits for carrying out the therapeutic methods or the assay methods of the invention are also contemplated herein as being within the invention, as are articles of manufacture that include compositions for use in the methods of the invention and instructions for the use thereof.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

Other features and advantages of the invention will be apparent from the following description of the preferred embodiments thereof and from the claims, taken in conjunction with the accompanying drawings, in which:

In FIG. 1A, Caco-2 cells were incubated for 24 or 48 h under control conditions or with graded concentrations (μmol/L) of either NAD+ (N) or adenosine (A). Fresh NAD+ was added to the wells after 24 h. CON indicates untreated monolayers and CYM indicates cytomix was added (n=6-12 per condition). In FIG. 1B, mice were injected at T=0 h with PBS or LPS and two injections of either PBS or NAD+ (132 mg/kg) dissolved in PBS. Ileal segments were harvested at T=18 h and permeability to FD4 measured. * indicates $p<0.05$ versus control; ** indicates $p<0.01$;

FIGS. 2A, 2B and 2C show the effect of extracellular NAD+ on the presence of ZO-1 and occludin in TJ complexes of Caco-2 cells. For FIG. 2A, cells were either left untreated (CON) or exposed to cytomix (CYM) in the absence or presence of 10 (N10) or 100 (N100) μmol/L NAD+ for 48 h. NP-40-insoluble protein was subjected to immunoprecipitation and Western blot analysis with an anti-ZO-1 or anti-occludin polyclonal antibody. For FIG. 2B, Caco-2 cells were exposed to cytomix (CYM) in the presence or absence of 10 μM adenosine (ADN). For FIG. 2C, Caco-2 cells were exposed to cytomix in the presence or absence of the indicated concentrations of cADPR. Western blots were repeated at least three times with reproducible results;

FIGS. 4A and 4B show increased production of NO. and iNOS expression caused by cytomix was inhibited in a concentration-dependent manner by the addition of extracellular NAD⁺. FIG. 4C show nuclear extracts were prepared from the cells 4 h after exposure to the agents (cytomix and NAD⁺), and these extracts were used in an electrophoretic mobility shift assay using the murine NF-κB site from the κ light chain promoter;

DETAILED DESCRIPTION OF THE INVENTION

During experiments designed to explore the biological effects of the decreased intracellular content of nicotinamide adenine dinucleotide (NAD⁺) in immunostimulated human Caco-2 enterocyte-like cells[11], it was serendipitously observed that adding NAD⁺ that was not protected by liposomes to the culture medium ameliorated derangements in epithelial barrier function that were induced by exposing these cells to a mixture of proinflammatory cytokines. Several recent studies have shown that certain cell types secrete NAD⁺[12,13] and/or respond to NAD⁺ in the extracellular milieu[12-19]. We have now discovered that NAD⁺ as a signaling molecule also exhibits anti-inflammatory properties, as described herein. Moreover, administration of NAD⁺ to mice ameliorates derangements in ileal mucosal barrier function induced by challenging the animals with lipopolysaccharide (LPS). Thus, according to the present invention, an NAD-related compound such as NAD⁺ or its cyclic derivative, cyclic ADP-ribose (cADPR), or analogues or derivatives thereof that activate the same anti-inflammatory pathway(s), can be administered to a patient in need of treatment as a method of preventing or treating conditions related to inflammation, such as intestine-specific conditions (e.g., Crohn's disease or ulcerative colitis) or systemic causes of inflammation (e.g., endotoxemia, sepsis, acute respiratory distress syndrome, rheumatoid arthritis, hemorrhagic shock/resuscitation or pancreatitis).

NAD⁺ is a ubiquitous cellular constituent that is used by cells as an electron acceptor (or, in its reduced form, NADH, as an electron donor) in a wide variety of enzyme-catalyzed redox reactions, such as those in the glycolytic pathway and the TCA cycle. Accumulating data suggest that NAD⁺ also functions as a signaling molecule[12-19]. In the experiments described herein, it is shown that extracellular NAD⁺ has another important signaling function. Specifically, it is shown that extracellular NAD⁺ preserves intestinal epithelial barrier function, e.g., when enterocyte-like Caco-2 cells are exposed to an inflammatory milieu, such as a mixture of proinflammatory cytokines (IFN-γ, IL-1β and TNF-α) or "cytomix." NAD⁺ also preserves the normal expression and localization of the TJ proteins ZO-1 and occludin in immunostimulated Caco-2 cells. Treatment with NAD⁺ decreased the nuclear translocation of NF-κB, prevented accumulation of iNOS mRNA and decreased the production of NO. in Caco-2 cells stimulated with proinflammatory cytokines. Taken together, these results show that NAD⁺ is acting as an anti-inflammatory agent.

The biological relevance of these ex vivo observations is emphasized by the results from in vivo studies, also described herein, showing that NAD⁺ can act as a pharmacological agent to ameliorate alterations in gut barrier function induced by injecting mice with LPS. Most dramatically, when used to treat mice challenged with a lethal dose of *Escherichia coli*, intravenous and intraperitoneal NAD⁺ (1 mg/kg pre-treatment, then 1 mg/kg every 6 h for five more doses) completely prevented mortality.

The ecto-NADases CD38 and CD157 are known to cyclize extracellular NAD⁺ to form cyclic ADP-ribose (cADPR) and nicotinamide[28,29]. Both proteins are expressed by a variety of cells and may exist as membrane bound receptors or in soluble form in the plasma of normal humans[29]. As described herein, extracellular cADPR, but not ADPR, also preserved the expression of occludin in immunostimulated Caco-2 cells. This observation suggests that extracellular NAD⁺ acts via the formation of cADPR, which can enter cells through either a CD38-dependent[31] or a CD38-independent mechanism[32]. Not being bound by any theory, it appears that cleavage and cyclization of NAD⁺ may be necessary for its anti-inflammatory effects, e.g., in Caco-2 cells in vitro or in endotoxemic mice, to be exerted. Thus, the NAD-related compound administered in the method of the invention is not packaged in liposomes, which would prevent the therapeutic compound from acting as a signaling molecule, but, instead, is administered to the patient in a form that is accessible to a receptor molecule, whether that molecule is soluble or membrane bound.

Normal circulating levels of NAD⁺ are 250±30 nmol/L and 140±10 nmol/L in humans and mice, respectively[44]. Thus, the normal circulating level of NAD⁺ is substantially less than the concentration required experimentally to preserve barrier function in immunostimulated Caco-2 monolayers. The effects of NAD⁺ may be exclusively pharmacological. Alternatively, high local concentrations of NAD⁺ could occur in vivo when the compound is released by cells in response to normal or pathological events. It is known, for example, that fibroblasts secrete NAD⁺[13], and fibroblasts are intimately associated with the basal side of the intestinal epithelial sheet[45].

As described herein, NAD⁺ and/or cADPR (or their functional analogues or derivatives) are capable of ameliorating structural and functional changes in cells affected by a proinflammatory milieu. The potent anti-inflammatory effects of these ubiquitous endogenous molecules suggest the existence of a receptor on the cell surface that can serve as a useful drug target, leading to the development of additional novel agents for the treatment of inflammatory conditions. Various ex vivo and in vivo assay systems are described herein for screening candidate therapeutic compounds for use in the method of the invention. A suitable assay system will have a measurement variable that is closely correlated with reduction in inflammation.

The first such in vitro assay system, described in Example II, is based on the recognition that a necessary function of the intestinal epithelium is the establishment of a selective barrier to allow the absorption of nutrients while restricting the uptake of toxic substances and microbes from the gut lumen. A major component of this epithelial barrier is the tight junction (TJ), a circumferential protein complex located at the apical/basolateral junction of opposing cells. Occludin[1] and claudins[2] are important TJ components that span the plasma membrane four times and are thought to make homotypic contacts with proteins in the plasma membrane of the opposing cell[3,4]. Thus, a candidate therapeutic compound having the effectiveness of NAD⁺ will be capable of restoring normal levels of these TJ components to test cells subjected to an inflammatory stimulus. The TJ complex is believed to be the point of cell-cell contact that presents the major barrier to paracellular transport[5,6]. Intestinal epithelial barrier function is compromised in a variety of inflammatory conditions including inflammatory bowel disease, cholestasis, hemorrhagic shock, and sepsis[7]. Alterations in intestinal epithelial barrier function have been implicated in the pathogenesis of inflammatory bowel disease and multiple organ system failure due to critical illness[7].

The second in vitro assay system, described in Example III, is based on measuring the release of inflammatory mediators (e.g., nitric oxide and TNF) from LPS-stimulated RAW 264.7 murine macrophage-like cells. LPS is a component of the cell wall of Gram-negative bacteria and has been implicated in the pathogenesis of sepsis and septic shock[46]. LPS has also been implicated in the pathogenesis of other serious conditions that are not associated with infection, such as cardiopulmonary bypass[47], alcoholic hepatitis[48], and inflammatory bowel disease[49]. When macrophages are exposed to LPS, a complex signaling cascade is initiated that ultimately leads to the transcriptional activation of numerous pro-inflammatory genes, including the genes encoding inducible nitric oxide synthase (iNOS) and TNF. In vitro, LPS-stimulated macrophages secrete NO. (produced from L-arginine in a reaction catalyzed by iNOS) and TNF among many other mediators. Thus, a convenient way to assess the anti-inflammatory activity of a test compound is to measure the effects of the compound on the amount of nitrite plus nitrate (end-products of NO. metabolism) and TNF in media conditioned by LPS-stimulated RAW 264.7 cells.

Figure 1A:
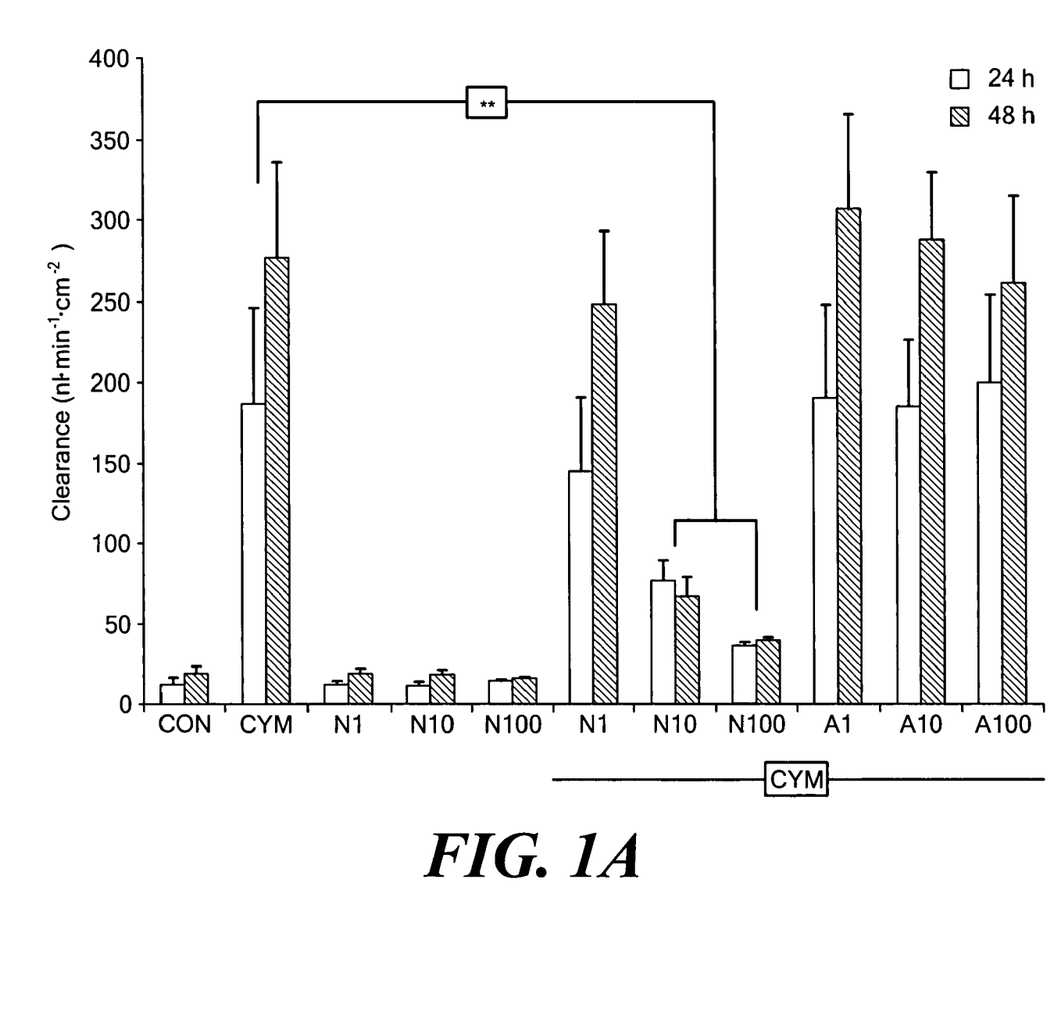
FIGS. 1A and 1B show the effect of extracellular NAD+ on the permeability of Caco-2 enterocytic monolayers and mouse ileal mucosa.
Figure 1B:
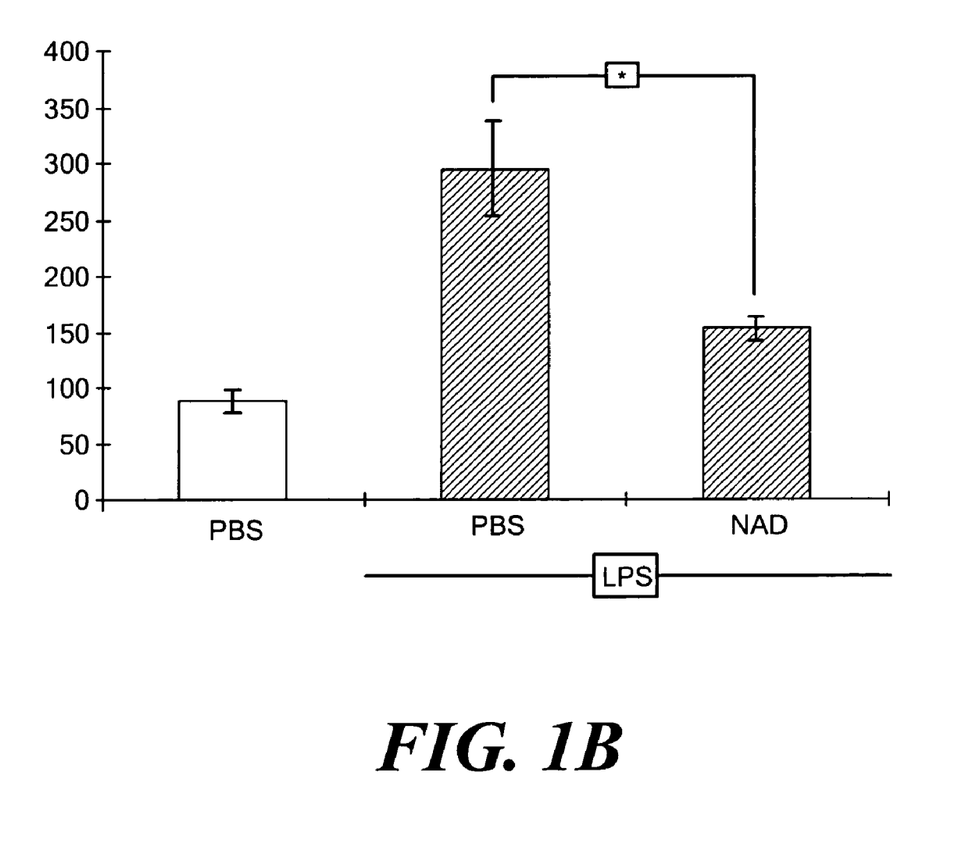

The in vivo assay system employed, shown in FIG. 1B of Example I, was based on the recognition that injecting mice with LPS leads to a systemic inflammatory response characterized by the release of myriad cytokines and other pro-inflammatory mediators. If the LPS dose is sufficiently large, this systemic inflammatory response is associated with cardiovascular failure and mortality. Thus, a convenient way to assess the anti-inflammatory activity of a test compound in vivo is to determine whether treatment with the agent can ameliorate LPS-induced mortality in mice. Acute endotoxemia in mice induced by injecting LPS is a reasonable model for certain forms of septic shock in humans (e.g., vascular collapse secondary to overwhelming meningococcal infection)[50]. More generally, agents such as various anti-TNF antibodies or anti-TNF fusion proteins that have been shown to ameliorate LPS-induced mortality in mice have been shown to be beneficial for the treatment of more chronic inflammatory conditions in patients, such as Crohn's disease or rheumatoid arthritis[51], supporting the reliability of the mouse model.

Extensive investigation has been carried out in recent years to identify oligonucleotide analogues that would be more stable in vivo and at least as active as their naturally occuring counterparts. Such activity, which is well-known to those of ordinary skill in the art, has also been conducted in an analogous fashion to provide active analogues or derivatives for the numerous functions of $NAD^+$ or cADPR[52]. Appropriate derivatives of the active compound in the composition according to the invention, tested, e.g., as described herein, include chemically synthesized derivatives of $NAD^+$ or cADPR, or synthetic or semi-synthetic $NAD^+$ or cADPR mimetics, that activate the same anti-inflammatory pathway(s). Acceptable derivatives may also be chemical variants that are known to improve stability and prolong the half-life of $NAD^+$ or cADPR, such as variants with replacements that stabilize phosphodiester linkages. For example, well-known anionic stabilizing replacements include sulfur (e.g., the phosphorothioates) or $BH_3$ for one or both non-chain phosphate oxygens. Neutral replacements include the methylphosphonates and peptide nucleic acid (PNA) derivatives, which are DNA mimetics in which the backbone of the molecule is composed of N-(2-aminoethyl)glycine rather than sugar-phosphate units. RNA analogues with conformationally locked sugar rings have also been described, as have N3'→P5' phosphoroamidate analogues[58]. For other chemical variants, $NAD^+$ can be covalently linked to albumin or attached to polyethylene glycol (PEG) moieties.

Acceptable variants can also include changes in the structure of the adenosine moiety, e.g., through various substituents at the ribose 2' position or by replacement of the ribose portion, e.g., with a modified cyclopentane structure[53,54] or by various substitutions at the ribose portion or the adenine portion[55]. Possible additional derivatives or analogues of $NAD^+$ include, but are not limited to, etheno-nicotinamide adenine dinucleotide[56], adenosine biphosphate analogues[53], benzamide adenine dinucleotide[57] and biotinylated or digoxigenin-labeled $NAD^{+56}$.

The therapeutic compositions in the methods of the invention may be administered orally (including enterally), topically, or parenterally (e.g., intranasally, subcutaneously, intramuscularly, intravenously, or intra-arterially) by routine methods in pharmaceutically acceptable inert carrier substances to address the inflammatory conditions described herein. For example, the compositions according to the method of the invention may be administered, either independently of accompanied by another anti-inflammatory agent, in a sustained release formulation using a biodegradable biocompatible polymer or in an enteric-coated formulation. An NAD-related compound according to the method of the invention can be administered, e.g., in a dosage of 0.25 µg/kg/day to 5 mg/kg/day, and preferably 1 µg/kg/day to 500 µg/kg/day. Optimal dosage and modes of administration can readily be determined by conventional protocols. Exemplary methods of providing $NAD^+$ or cADPR in drug form can be found in Matteucci, M., Oligonucleotide Analogues: An Overview. *Ciba Found Symp* (1997) 209: 5-14, discussion 14-18.

EXAMPLES

The following examples are presented to illustrate the advantages of the present invention and to assist one of ordinary skill in making and using the same. These examples are not intended in any way otherwise to limit the scope of the disclosure.

Materials and Methods

Reagents. All chemicals were from Sigma-Aldrich Chemical Co. (St. Louis, Mo.) unless otherwise noted. Recombinant human cytokines were obtained from Pierce-Endogen (Rockford, Ind.).

Animals. This research complied with regulations regarding animal care as published by the National Institutes of Health and was approved by the Institutional Animal Use and Care Committee of the University of Pittsburgh. Male 7-8 week old C57Bl/6J mice weighing 20-25 g were from Jackson Laboratories (Bar Harbor, Me.). To induce a systemic inflammatory response, mice were injected intraperitoneally (IP) with *Escherichia coli* (strain O111:B4) LPS (17 mg/kg) dissolved in 1.0 ml of PBS. Control animals were injected with a similar volume of PBS. Some mice were treated with an intravenous (IV) injection (100 μL) of either PBS or 132 mg/kg NAD+ in PBS given 5 min before LPS or PBS injection, and this injection was repeated IP 12 h later. Groups of mice were anesthetized with 60-90 mg/kg sodium pentobarbital 18 h after the first injection with PBS or LPS. Segments of ileum were harvested to assess mucosal permeability to FD4 using an ex vivo everted gut sac method as previously described.[20]

Cell Culture. Caco-2 human enterocyte-like cells were routinely maintained at 37° C. in DMEM with 10% FBS, as described by Han et al.[9] All cells were fed by changing the cell culture medium twice per week. For experiments, cells were grown on Transwell inserts (0.4 μm pore size; Corning Costar Corp., Cambridge, Mass.) and used 14-17 days post-confluence. Paracellular permeability of Caco-2 monolayers was measured by determining the apical to basal clearance of FD4 (25 mg/mL), as described by Han et al.[9] For some experiments, the mouse RAW 264.7 cell line was used, which is functionally and morphologically similar to murine monocytes.

Immunoprecipitation and Western blotting. Western blots were performed as described [9]. Briefly, Caco-2 cells were left unstimulated or exposed to various agents. Cells were lysed in 1 mL of ice-cold NP-40-lysis buffer (25 mmol/L HEPES, pH 7.4, 150 mmol/L NaCl, 4 mmol/L EDTA, 25 mmol/L NaF, 1% NP-40, 1 mmol/L $Na_3VO_4$, 1 mmol/L APMSF, 10 μg/mL leupeptin, 10 μg/mL aprotinin) and insoluble material was collected by centrifugation and designated the NP-40 insoluble fraction. This pellet was dissolved in 100 μL of SDS-buffer (25 mmol/L HEPES, pH 7.5, 4 mmol/L EDTA, 25 mmol/L NaF, 1% SDS, 1 mmol/L $Na_3VO_4$) then diluted to 1 mL with NP-40-lysis buffer. The proteins were immunoprecipitated to concentrate the antigen prior to Western blotting. Both steps were performed using anti-ZO-1 or anti-occludin polyclonal antibody from Zymed (South San Francisco, Calif.). Horseradish peroxidase-conjugated secondary antibodies were from Jackson ImmunoResearch Laboratories, Inc. (West Grove, Pa.). Blots were developed with the Enhanced Chemiluminescence substrate (Amersham, Piscataway, N.J.).

Immunofluorescence. All procedures were performed at 0-4° C. as described.[9] Caco-2 cells growing on 24 well clear Transwell inserts were fixed and stained with a mouse anti-ZO-1 monoclonal antibody (mAb; BD Translabs, Franklin Lakes, N.J.) and rabbit an anti-occludin polyclonal antibody diluted 1:100. The secondary antibodies were 5 μg/mL FITC-conjugated affinity-purified donkey anti-mouse IgG and 15 μg/mL TRITC-conjugated affinity-purified goat anti-rabbit IgG (Jackson ImmunoResearch Laboratories).

Measurement of NO. production and iNOS gene expression. NO. production[21] was measured and RT-PCR [22] for iNOS mRNA and 18S RNA were performed as described. The gels were captured using an imaging workstation (NucleoVision), and quantified with GelExpert™ 3.5. Relative expression of iNOS is reported after normalizing for 18S loading in FIG. 4B.

Electrophoretic mobility shift assay (EMSA). Nuclear extracts were prepared and analyzed as described.[23] However, 38.3 μL of 10% NP-40 was used to lyse the cells, the nuclei were isolated by centrifugation at 310 g for 3 min, and the nuclear pellets were resuspended in 80 μL of Buffer II.

Statistical Analysis: Results are presented as means ± SEM. Data were analyzed using analysis of variance (ANOVA). P values <0.05 were considered significant.

Example I

Extracellular NAD+ Preserves Intestinal Epithelial Barrier Function ex vivo and in vivo Caco-2 monolayers growing on permeable supports were left untreated or exposed to cytomix for 24 or 48 h in the absence or presence of graded concentrations of NAD+ or adenosine. Paracellular permeability was determined by measuring the apical-to-basolateral flux of FD4. Epithelial permeability was unaffected when monolayers were incubated with NAD+ alone. Exposing Caco-2 cells to cytomix increased the clearance of FD4 across the monolayers (FIG. 1A). Addition of NAD+ ameliorated cytomix-induced epithelial hyperpermeability in a concentration-dependent manner. The protection afforded by 10 and 100 μmol/L NAD+ was statistically significant.

NAD+ is structurally related to a nucleoside, adenosine, that is known to exert anti-inflammatory effects by binding to certain purinergic receptors;[24] accordingly, the possibility that activation of a receptor for adenosine was responsible for the amelioration of cytokine-induced hyperpermeability by NAD+ was considered. To investigate this idea, Caco-2 monolayers were exposed to cytomix in the absence or presence of 10 μmol/L adenosine (FIG. 1A). Adenosine had no effect on the induction of hyperpermeability by cytomix, suggesting that NAD+ was not simply an adenosine mimetic.

In the setting of systemic inflammation, circulating blood monocytes often encounter lipopolysaccharide (LPS), a potent inflammatory molecule derived from the outer surface of Gram-negative bacteria. To determine whether treatment with NAD+ preserves intestinal mucosal barrier function in vivo, mice were injected IP with LPS (17 mg/kg) suspended in PBS (1 mL) to stimulate endotoxic shock or with a similar volume of the PBS vehicle alone as a control. Ileal segments were harvested 18 h later, and an ex vivo everted gut sac technique was used to measure mucosal permeability to FD4. Some mice were treated with two 132 mg/kg doses of NAD+. Other mice were injected with similar volumes of the PBS vehicle. As expected,[25] injecting mice with LPS caused a significant increase in mucosal permeability to FD4 whereas treatment with two doses of NAD+ significantly ameliorated the increase in mucosal permeability induced by LPS in mice (FIG. 1B).

Example II

Figure 2A:
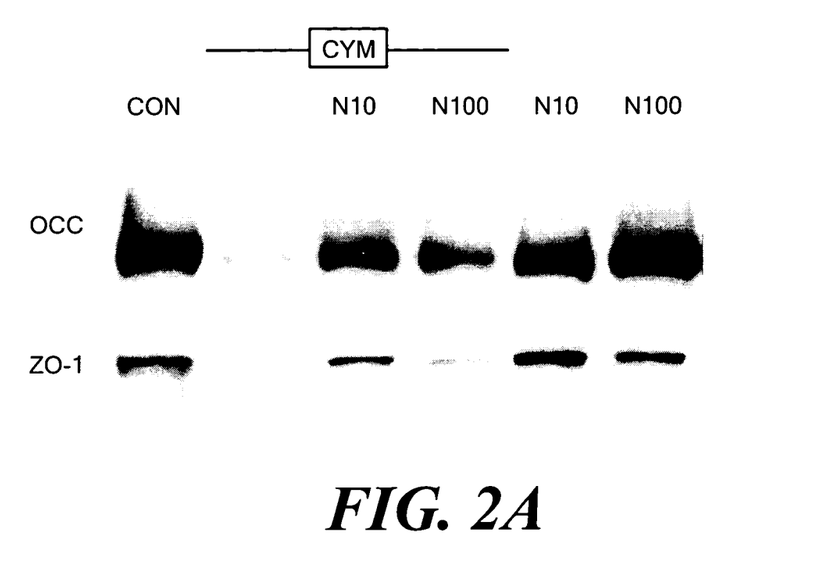

Extracellular NAD+ Ameliorates Derangements in TJ Protein Expression and Cellular Localization Caused by Cytomix Proinflammatory cytokines are known to alter the expression and localization of several TJ proteins in cultured intestinal epithelial cells, including occludin, claudin-1 and ZO-1.[9,10] Whether NAD+ preserves the expression and targeting of TJ proteins in cells that were exposed to cytomix was tested. Caco-2 cells were grown in the absence or presence of cytomix or NAD+, and NP-40-insoluble protein complexes were isolated after 48 h. The insoluble complexes, which represent insoluble cytoskeletal proteins and associated TJ proteins,[26,27] were solubilized with SDS and subjected to immunoprecipitation followed by immunoblotting with anti-occludin or anti-ZO-1 antibodies. Exposure to cytomix for 48 h markedly decreased the amounts of occludin and ZO-1 present in TJs (FIG. 2A). When cells were simultaneously incubated with cytomix and 10 or 100

μmol/L NAD⁺, normal levels of these proteins were present in NP-40-insoluble complexes.

Figure 2B:
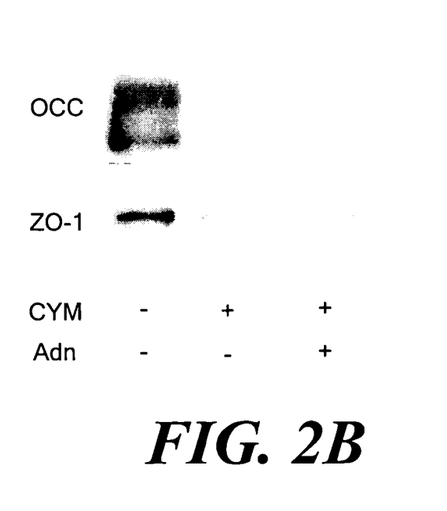

To again exclude the possibility that NAD⁺ was acting as an adenosine mimetic, NP-40-insoluble extracts were prepared from Caco-2 cells that were untreated or exposed to cytomix for 48 h in the absence or presence of 10 μM adenosine. Adenosine failed to prevent the decrease in NP-40-insoluble occludin or ZO-1 in Caco-2 cells exposed to cytomix (FIG. 2B).

Figure 3:
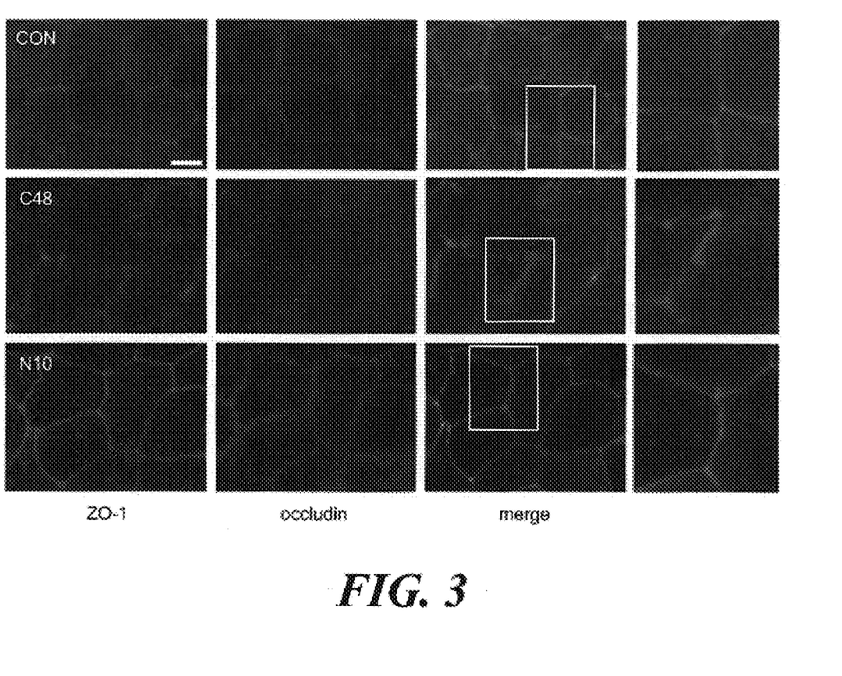
FIG. 3 shows immunofluorescent microscopy of the effect of NAD+ on ZO-1 (green) and occludin (red) localization in Caco-2 cells exposed to cytomix. Caco-2 cells were either left untreated (CON) or exposed to cytomix for 48 h (C48). Some cells were exposed to cytomix for 48 h and treated at 0 and 24 h with 10 μM NAD+ (N10). Distribution and colocalization of ZO-1 (green) and occludin (red) was disrupted, and this was blocked by NAD+. Magnification is 1000× in the left three columns, and 2000× in the right column showing detailed of the boxed regions. The bar is 10 μm.

Immunofluorescence microscopy was used to assess the structure of TJs in Caco-2 cells grown on Transwells. The cells were either left untreated (FIG. 3; Panel CON) or exposed to cytomix for 48 h in the absence (Panel C48) or presence (Panel N10) of extracellular NAD⁺ (10 μmol/L added at 0 and 24 h). The cells were permeabilized, fixed, and stained using FITC- and TRITC-conjugated antibodies directed against ZO-1 and occludin, respectively. In control confluent Caco-2 monolayers, these proteins both were predominantly localized to regions near cell-cell boundaries. Staining was even and continuous. Following treatment with cytomix, dispersed lesions appeared throughout the monolayer, in which immunostaining for ZO-1 at cell boundaries became faint, diffuse, and discontinuous. Exposure to cytomix also was associated with "ruffling" of ZO-1 and occludin immunostaining. Monolayers that were exposed to cytomix in the presence of 10 μmol/L NAD⁺ showed continuous staining of ZO-1 and occludin at cell-cell boundaries. However, some ruffling of the staining pattern was still evident.

Example III

Figure 2C:
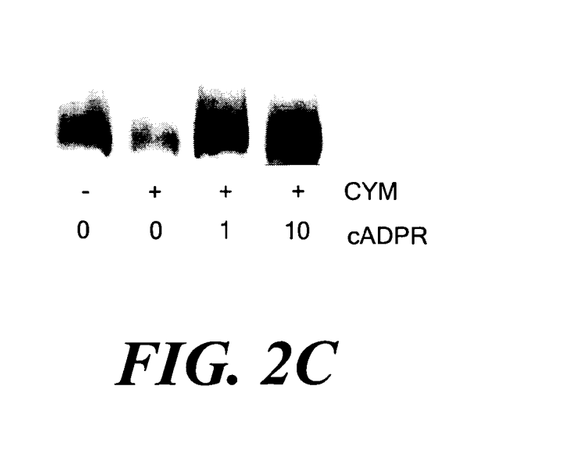

Extracellular cADPR Ameliorates Derangements in TJ Protein Expression and Cellular Localization Caused by Cytomix In other systems, the signaling effects of NAD⁺ are dependent on its conversion to cyclic ADP-ribose (cADPR)[28,29]. Therefore, the effects of extracellular cADPR on cytomix-induced alterations in occludin expression were evaluated. Co-incubating cells with 10 or 100 μmol/L cADPR preserved expression of occludin in Caco-2 cells exposed to cytomix (FIG. 2C). Remarkably, these concentrations of cADPR increased the expression of occludin to greater than baseline levels in immunostimulated Caco-2 cells. This effect of cADPR was specific for the cyclic nucleoside, since similar concentrations of (non-cyclic) ADP-ribose failed to preserve occludin expression in immunostimulated Caco-2 cells.

Example IV

Extracellular NAD⁺ Decreases iNOS Expression in Immunostimulated Cells

Changes in epithelial permeability caused by exposure to proinflammatory cytokines are due, at least in part, to excessive production of nitric oxide (NO.)[9,30]. LPS and cytomix induce the expression of inducible nitric oxide synthase (iNOS) in RAW monocyte-like cells and Caco-2 enterocyte-like cells, respectively. Upregulation of iNOS leads to the production of NO. NO. produced by myeloid cells is bactericidal, and the NO. generated by enterocytes appears to be involved in the regulation of cell-cell contacts (tight junctions), which are important for the integrity of the epithelial sheet.

Figure 4A:
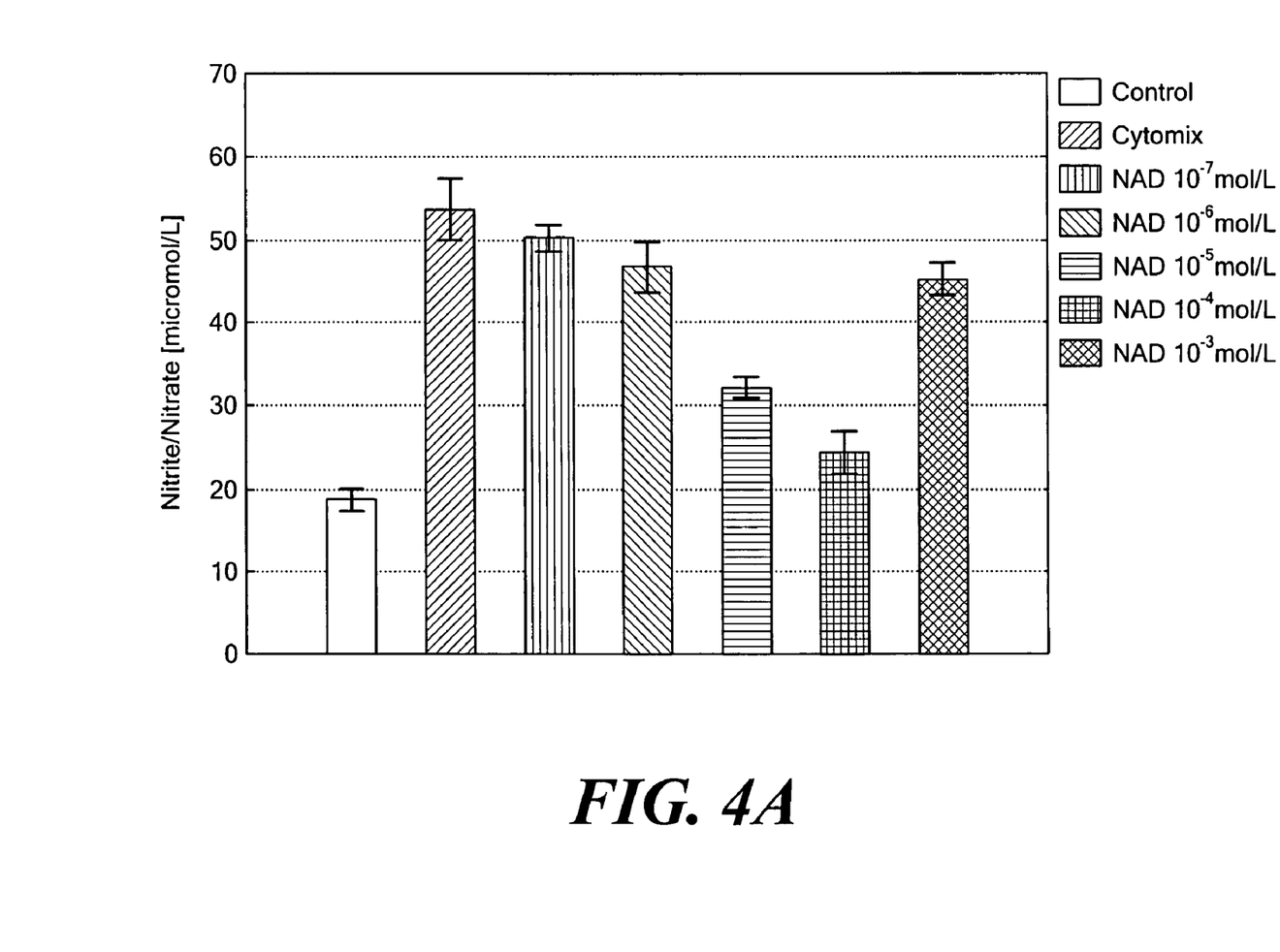
FIGS. 4A, 4B and 4C show the effect of NAD+ on cytomix-induced NO. production, inducible nitric oxide synthase (iNOS) expression and NF-κB activation.
Figure 4B:
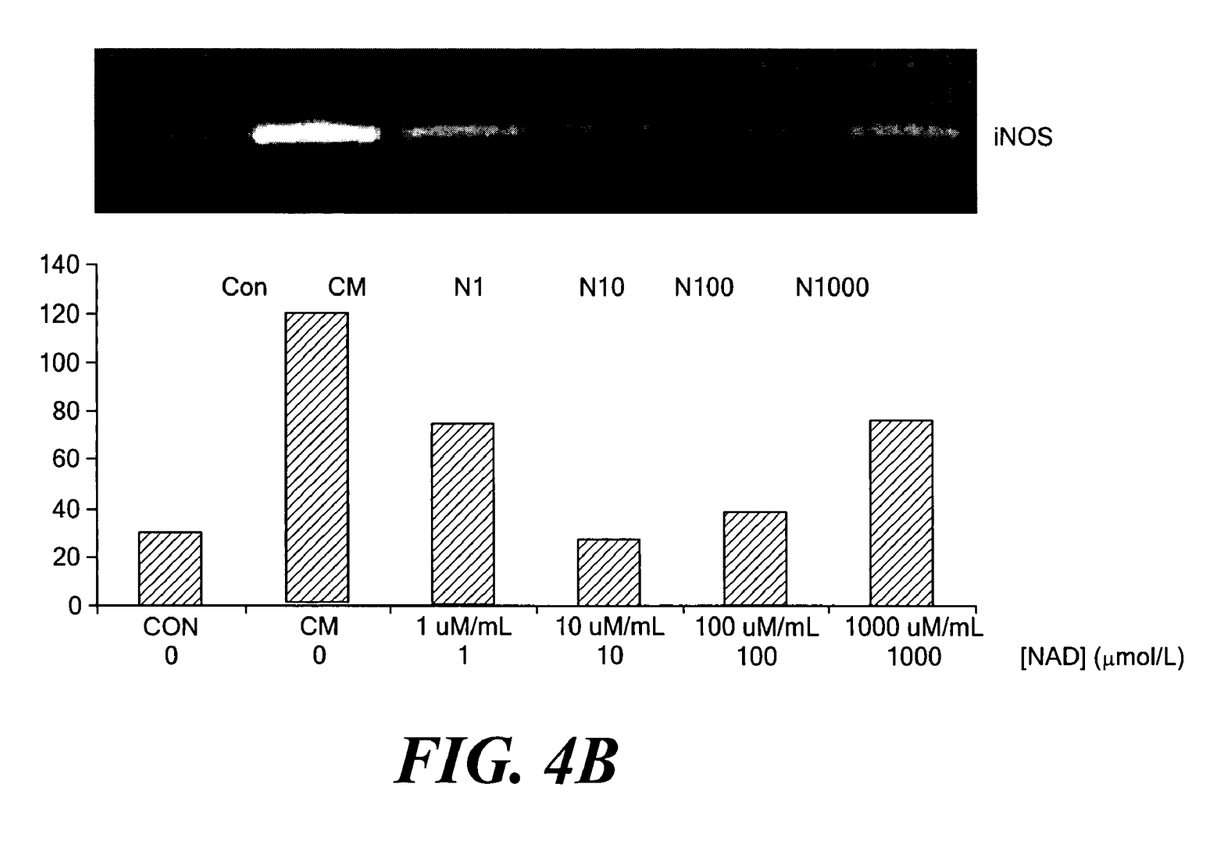

Accordingly, it was determined whether NAD⁺ decreased the production of NO. (as assessed by measuring $NO_2^-$ and $NO_3^-$ in culture supernatants) by Caco-2 cells exposed to cytomix (similar study using RAW monocyte-like cells is not shown). As expected, cytomix increased the production of NO., but this effect was inhibited in a concentration-dependent manner by the addition of extracellular NAD⁺ (FIG. 4A). Maximal inhibition was observed using 100 μmol/L NAD⁺; inhibition was decreased when NAD⁺ was increased to 1000 μmol/L. Cytomix increased expression of inducible nitric oxide synthase (iNOS) mRNA (FIG. 4B), and NAD⁺ blocked this effect. Again, there was a biphasic response to NAD⁺ treatment; provided maximal inhibition and higher doses inhibited less well. Thus, another inflammatory response, namely the induction of iNOS gene expression and the concomitant production of NO., is blocked by extracellular NAD⁺ in both myeloid and epithelial cells.

Example V

Figure 4C:
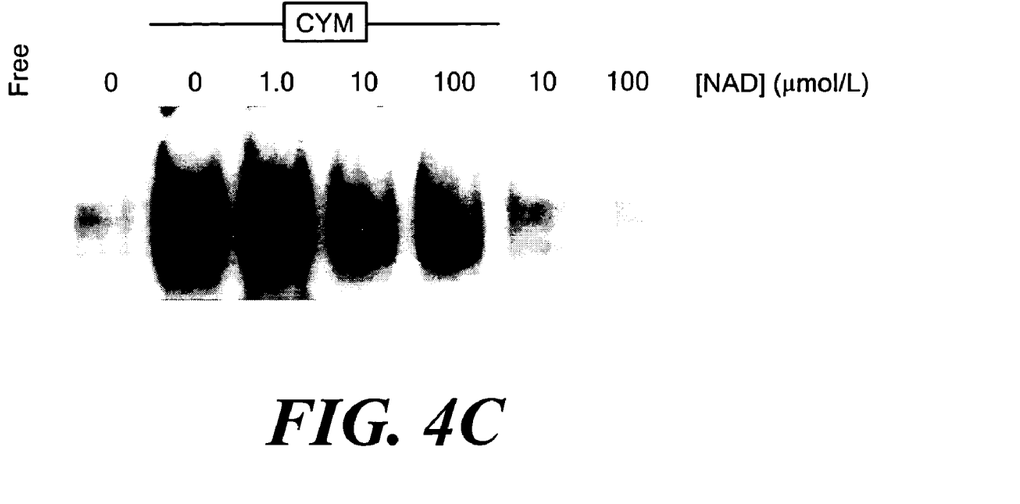

Extracellular NAD⁺ Inhibits the Activation of NF-κB iNOS induction is dependent, in part, on activation of the transcription factor NF-κB, a transcription factor that is required for a variety of monocyte inflammatory responses, e.g., to LPS. Therefore, we tested the ability of NAD⁺ to inhibit DNA binding by NF-κB in Caco-2 cells exposed to cytomix. Treatment of immunostimulated cells with 1 μmol/L NAD⁺ had no effect on cytomix-induced NF-κB activation, but co-incubation of cells with 10 or 100 μmol/L NAD⁺ clearly decreased NF-κB DNA binding (FIG. 4C) in nuclear extracts. NAD⁺ alone had no effect on the nuclear levels of NF-κB.

Additional studies were performed to show the potent anti-inflammatory capacity of extracellular NAD⁺. RAW 264.7 cells in tissue culture dishes were stimulated with LPS prepared from *Escherichia coli* strain 011:B4, and the activation of NF-κB was measured. Some cells were exposed to 10 ng/ml LPS in the presence of 1-100 μM NAD. Nuclear proteins were extracted from the cells 15 min after exposure to the compounds, and NF-κB levels were determined using the electrophoretic mobility shift assay.

Figure 5:
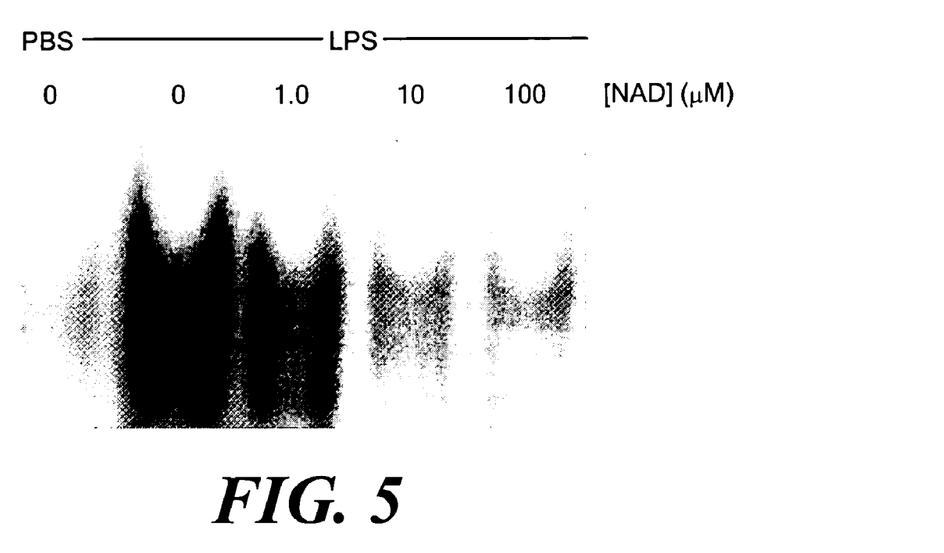
FIG. 5 is an immunofluorescent micrograph showing that extracellular NAD⁺ blocks the activation of NF-κB in RAW cells exposed to 10 ng/ml LPS.

The addition of LPS greatly increased nuclear levels of NF-κB, as shown in FIG. 5 (compare lanes 1 and 2). However, the addition of as little as 1 μM NAD⁺ to LPS treated cells dramatically decreased the nuclear localization of NF-κB (see, FIG. 5, lanes 3-5). The highest dose of NAD⁺ tested (100 μM NAD⁺) decreased nuclear NF-κB levels to near baseline levels. Thus, very low doses of extracellular NAD⁺ can effectively block the activation of NF-κB, an important transcription factor mobilized during an inflammatory response.

Example VI

NAD⁺ as an Anti-Inflammatory Agent—TNF-α Study

Figure 6:
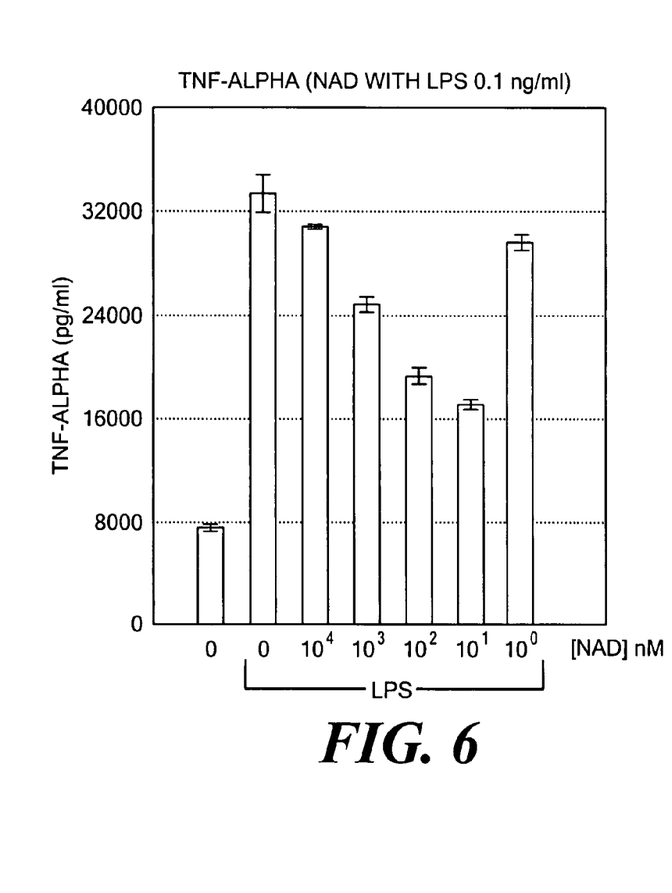
FIG. 6 is a graph showing that extracellular NAD⁺ blocks the release of TNF-α by RAW cells exposed to LPS.

Whether NAD⁺ could prevent the production of tumor necrosis factor α (TNF-α), a potent proinflammatory cytokine produced by activated monocytes and macrophages, was tested. Supernatants were collected from RAW cells treated with LPS in the absence or presence of NAD⁺. TNF-α levels were quantitated by ELISA. As shown in FIG. 6, as little as 1 μM NAD⁺ partially blocked the LPS-induced release of TNF-α from RAW cells.

Example VII

NAD⁺ as an Anti-Inflammatory Agent—Mortality Study

Figure 7:
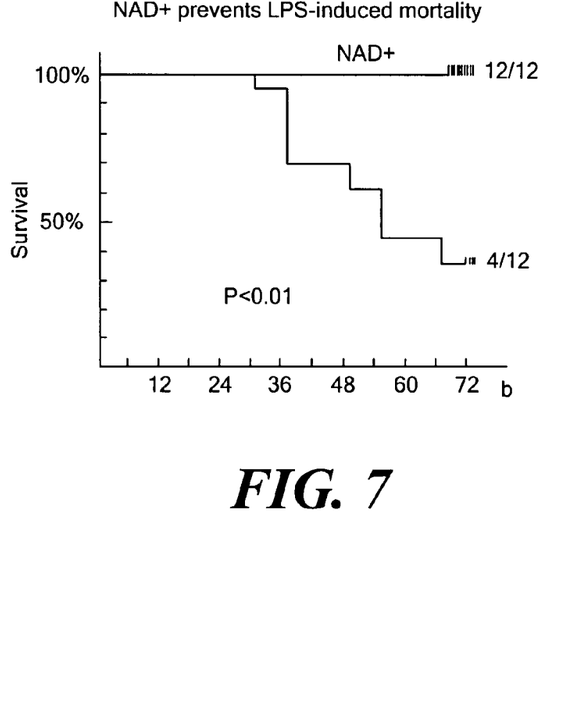
FIG. 7 is a graph showing the effect of NAD⁺ in preventing LPS-induced mortality in a mouse model.

NAD$^+$ was used to treat mice challenged with a lethal dose of *Escherichia coli* (O111:B4 LPS; 17 mg/kg). As shown in FIG. 7, intravenous and intraperitoneal NAD$^+$, at a dosage regimen of 1 mg/kg pre-treatment and then 1 mg/kg every 6 h for five more doses, completely prevented mortality.

REFERENCES

1. Furuse M, Hirase T, Itoh M, Nagafuchi A, Yonemura S, Tsukita S. Occludin: a novel integral membrane protein localizing at tight junctions. J Cell Biol 1993; 123: 1777-88.
2. Furuse M, Fujita K, Hiiragi T, Fujimoto K, Tsukita S. Claudin-1 and -2: novel integral membrane proteins localizing at tight junctions with no sequence similarity to occludin. J Cell Biol 1998; 141: 1539-50.
3. Sonoda N, Furuse M, Sasaki H, Yonemura S, Katahira J, Horiguchi Y, Tsukita S. Clostridium perfringens enterotoxin fragment removes specific claudins from tight junction strands: Evidence for direct involvement of claudins in tight junction barrier. J Cell Biol 1999; 147: 195-204.
4. Wong V, Gumbiner B M. A synthetic peptide corresponding to the extracellular domain of occludin perturbs the tight junction permeability barrier. J Cell Biol 1997; 136: 399-409.
5. Gumbiner B M. Breaking through the tight junction barrier. J Cell Biol 1993; 123: 1631-3.
6. Anderson J M, Van Itallie C M. Tight junctions and the molecular basis for regulation of paracellular permeability. Am J Physiol 1995; 269: G467-75.
7. Unno N, Fink M P. Intestinal epithelial hyperpermeability. Mechanisms and relevance to disease. Gastroenterol Clin North Am 1998; 27: 289-307.
8. Zolotarevsky Y, Hecht G, Koutsouris A, Gonzalez D E, Quan C, Tom J, Mrsny R J, Turner J R. A membrane-permeant peptide that inhibits MLC kinase restores barrier function in in vitro models of intestinal disease. Gastroenterology 2002; 123: 163-72.
9. Han X, Fink M P, Delude R L. Proinflammatory cytokines cause NO.-dependent and independent changes in expression and localization of tight junction proteins in intestinal epithelial cells. Shock 2003; 19: 229-37.
10. Youakim A, Ahdieh M. Interferon-gamma decreases barrier function in T84 cells by reducing ZO-1 levels and disrupting apical actin. Am J Physiol 1999; 276: G1279-88.
11. Khan A U, Delude R L, Han Y Y, Sappington P L, Han X, Carcillo J A, Fink M P. Liposomal NAD$^+$ prevents diminished O$_2$ consumption by immunostimulated Caco-2 cells. Am J Physiol Lung Cell Mol Physiol 2002; 282: L1082-91.
12. Romanello M, Padoan M, Franco L, Veronesi V, Moro L, D'Andrea P. Extracellular NAD$^+$ induces calcium signaling and apoptosis in human osteoblastic cells. Biochem Biophys Res Commun 2001; 285: 1226-31.
13. Bruzzone S, Franco L, Guida L, Zocchi E, Contini P, Bisso A, Usai C, De Flora A. A self-restricted CD38-connexin 43 cross-talk affects NAD$^+$ and cyclic ADP-ribose metabolism and regulates intracellular calcium in 3T3 fibroblasts. J Biol Chem 2001; 276: 48300-8.
14. Currie K P, Swann K, Galione A, Scott R H. Activation of Ca$^{2+}$-dependent currents in cultured rat dorsal root ganglion neurones by a sperm factor and cyclic ADP-ribose. Mol Biol Cell 1992; 3: 1415-25.
15. Takasawa S, Nata K, Yonekura H, Okamoto H. Cyclic ADP-ribose in insulin secretion from pancreatic beta cells. Science 1993; 259: 370-3.
16. Morrissette J, Heisermann G, Cleary J, Ruoho A, Coronado R. Cyclic ADP-ribose induced Ca$^{2+}$ release in rabbit skeletal muscle sarcoplasmic reticulum. FEBS Lett 1993; 330: 270-4.
17. Beers K W, Chini E N, Lee H C, Dousa T P. Metabolism of cyclic ADP-ribose in opossum kidney renal epithelial cells. Am J Physiol 1995; 268: C741-6.
18. Lilly L B, Gollan J L. Ryanodine-induced calcium release from hepatic microsomes and permeabilized hepatocytes. Am J Physiol 1995; 268: G1017-24.
19. Guse A H, da Silva C P, Emmrich F, Ashamu G A, Potter B V, Mayr G W. Characterization of cyclic adenosine diphosphate-ribose-induced Ca$^{2+}$ release in T lymphocyte cell lines. J Immunol 1995; 155: 3353-9.
20. Yang R, Gallo D J, Baust J J, Uchiyama T, Watkins S K, Delude R L, Fink M P. Ethyl pyruvate modulates inflammatory gene expression in mice subjected to hemorrhagic shock. Am J Physiol Gastrointest Liver Physiol 2002; 283: G212-21.
21. Vodovotz Y. Modified microassay for serum nitrite and nitrate. Biotechniques 1996; 20: 390-2, 394.
22. Sappington P L, Yang R, Yang H, Tracey K J, Delude R L, Fink M P. HMGB1 B box increases the permeability of Caco-2 enterocytic monolayers and impairs intestinal barrier function in mice. Gastroenterology 2002; 123: 790-802.
23. Delude R L, Fenton M J, Savedra R, Jr., Perera P Y, Vogel S N, Thieringer R, Golenbock D T. CD14-mediated translocation of nuclear factor-κB induced by lipopolysaccharide does not require tyrosine kinase activity. J Biol Chem 1994; 269: 22253-60.
24. Sajjadi F G, Takabayashi K, Foster A C, Domingo R C, Firestein G S. Inhibition of TNF-alpha expression by adenosine: role of A3 adenosine receptors. J Immunol 1996; 156: 3435-42.
25. Sappington P L, Han X, Yang R, Delude R L, Fink M P. Ethyl pyruvate ameliorates intestinal epithelial barrier dysfunction in endotoxemic mice and immunostimulated Caco-2 enterocytic monolayers. J Pharmacol Exp Ther 2003; 304: 464-76.
26. Wong V. Phosphorylation of occludin correlates with occludin localization and function at the tight junction. Am J Physiol 1997; 273: C1859-67.
27. Sakakibara A, Furuse M, Saitou M, Ando-Akatsuka Y, Tsukita S. Possible involvement of phosphorylation of occludin in tight junction formation. J Cell Biol 1997; 137: 1393-401.
28. Okamoto H, Takasawa S. Recent advances in the Okamoto model: the CD38-cyclic ADP-ribose signal system and the regenerating gene protein (Reg)-Reg receptor system in beta-cells. Diabetes 2002; 51 Suppl 3: S462-73.
29. Deaglio S, Mehta K, Malavasi F. Human CD38: a (r)evolutionary story of enzymes and receptors. Leuk Res 2001; 25: 1-12.
30. Unno N, Menconi M J, Smith M, Fink M P. Nitric oxide mediates interferon-gamma-induced hyperpermeability in cultured human intestinal epithelial monolayers. Crit Care Med 1995; 23: 1170-6.
31. Franco L, Guida L, Bruzzone S, Zocchi E, Usai C, De Flora A. The transmembrane glycoprotein CD38 is a catalytically active transporter responsible for generation and influx of the second messenger cyclic ADP-ribose across membranes. Faseb J 1998; 12: 1507-20.
32. Franco L, Zocchi E, Usai C, Guida L, Bruzzone S, Costa A, De Flora A. Paracrine roles of NAD+ and cyclic ADP-ribose in increasing intracellular calcium and enhancing cell proliferation of 3T3 fibroblasts. J Biol Chem 2001; 276: 21642-8.
33. Verderio C, Bruzzone S, Zocchi E, Fedele E, Schenk U, De Flora A, Matteoli M. Evidence of a role for cyclic ADP-ribose in calcium signalling and neurotransmitter release in cultured astrocytes. J Neurochem 2001; 78: 646-57.
34. Zocchi E, Podesta M, Pitto A, Usai C, Bruzzone S, Franco L, Guida L, Bacigalupo A, De Flora A. Paracrinally stimulated expansion of early human hemopoietic progenitors by stroma-generated cyclic ADP-ribose. Faseb J 2001; 15: 1610-2.
35. Franco L, Bruzzone S, Song P, Guida L, Zocchi E, Walseth T F, Crimi E, Usai C, De Flora A, Brusasco V. Extracellular cyclic ADP-ribose potentiates ACh-induced contraction in bovine tracheal smooth muscle. Am J Physiol Lung Cell Mol Physiol 2001; 280: L98-L106.
36. Lund F E, Muller-Steffner H M, Yu N, Stout C D, Schuber F, Howard M C. CD38 signaling in B lymphocytes is controlled by its ectodomain but occurs independently of enzymatically generated ADP-ribose or cyclic ADP-ribose. J Immunol 1999; 162: 2693-702.
37. Esguerra M, Miller R F. CD38 expression and $NAD^+$-induced intracellular $Ca^+$ mobilization in isolated retinal Muller cells. Glia 2002; 39: 314-9.
38. Barone F, Genazzani A A, Conti A, Churchill G C, Palombi F, Ziparo E, Sorrentino V, Galione A, Filippini A. A pivotal role for cADPR-mediated $Ca^{2+}$ signaling: regulation of endothelin-induced contraction in peritubular smooth muscle cells. Faseb J 2002; 16: 697-705.
39. Hedeskov C J. Mechanism of glucose-induced insulin secretion. Physiol Rev 1980; 60: 442-509.
40. Takasawa S, Tohgo A, Noguchi N, Koguma T, Nata K, Sugimoto T, Yonekura H, Okamoto H. Synthesis and hydrolysis of cyclic ADP-ribose by human leukocyte antigen CD38 and inhibition of the hydrolysis by ATP. J Biol Chem 1993; 268: 26052-4.
41. Kato I, Takasawa S, Akabane A, Tanaka O, Abe H, Takamura T, Suzuki Y, Nata K, Yonekura H, Yoshimoto T, et al. Regulatory role of CD38 (ADP-ribosyl cyclase/cyclic ADP-ribose hydrolase) in insulin secretion by glucose in pancreatic beta cells. Enhanced insulin secretion in CD38-expressing transgenic mice. J Biol Chem 1995; 270: 30045-50.
42. Tohgo A, Munakata H, Takasawa S, Nata K, Akiyama T, Hayashi N, Okamoto H. Lysine 129 of CD38 (ADP-ribosyl cyclase/cyclic ADP-ribose hydrolase) participates in the binding of ATP to inhibit the cyclic ADP-ribose hydrolase. J Biol Chem 1997; 272: 3879-82.
43. Duncan R L, Turner C H. Mechanotransduction and the functional response of bone to mechanical strain. Calcif Tissue Int 1995; 57: 344-58.
44. Kim U H, Kim M K, Kim J S, Han M K, Park B H, Kim H R. Purification and characterization of NAD glycohydrolase from rabbit erythrocytes. Arch Biochem Biophys 1993; 305: 147-52.
45. Parker F G, Barnes E N, Kaye G I. The pericryptal fibroblast sheath. IV. Replication, migration, and differentiation of the subepithelial fibroblasts of the crypt and villus of the rabbit jejunum. Gastroenterology 1974; 67: 607-21.
46. Opal S M. The clinical relevance of endotoxin in human sepsis: a critical analysis. J Endotoxin Res 8: 473-476, 2003.
47. Bennett-Guerrero E, Ayuso L, Hamilton-Davies C, White W D, Barclay G R, Smith P K, King S A, Muhlbaier L H, Newman M F and Mythen M G. Relationship of preoperative antiendotoxin core antibodies and adverse outcomes following cardiac surgery. J Amer Med Assoc 277: 646-650, 1997.
48. Tamai H, Kato S, Horie Y, Ohki E, Yokoyama H and Ishii H. Effect of acute ethanol administration on the intestinal absorption of endotoxin in rats. Alcohol Clin Exp Res 24: 390-394, 2000.
49. Caradonna L, Amati L, Magrone T, Pellegrino N M, Jirillo E and Caccavo D. Enteric bacteria, lipopolysaccharides and related cytokines in inflammatory bowel disease: biological and clinical significance. J Endotoxin Res 6: 205-214, 2000.
50. Fink M P and Heard S O. Research review: laboratory models of sepsis and septic shock. J Surg Res 49: 186-196, 1990.
51. Tracey K J and Abraham E. From mouse to man: or what have we learned about cytokine-based anti-inflammatory therapies? Shock 11: 224-225, 1999.
52. Matteucci, M. Oligonucleotides as Therapeutic Agents, Wiley, Chichester (Ciba Foundation Symposium 209) 1997, pp. 5-18.
53. Boyer et al., Brit. J. Pharmacol. (2002) 135, 2004-2010.
54. Hernandez et al., Bioorganic & Med. Chem. (2002) 10, 2723-2730.
55. Kennedy et al., Bioorganic & Med. Chem. Letters (2001) 11, 95-98.
56. Davis et al., J. Histochem. & Cytochem. (1998) 46, 1279-1289), adenosine biphosphate analogues.
57. Szekeres et al., Curr. Med. Chem. (2002) 9, 759-764.
58. Egli et al., Cell. Mol. Life Sci. (2000) 57, 1440-1456.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method for treating an inflammatory condition, said method comprising the steps of:
   providing a patient having an inflammatory condition; and
   administering to said patient a therapeutically effective amount of a composition comprising a compound selected from the group consisting of cyclic adenosine diphosphate ribose (cADPR), cADPR having a stabilized phosphodiester linkage replacement, cADPR having a conformationally locked sugar ring and cADPR having a N3'→P5" phosphoroamidate replacement, wherein said compound is in a form that is accessible to a receptor molecule, wherein said composition is conveyed in a pharmaceutically acceptable carrier vehicle and wherein said composition reduces the degree of said inflammatory condition in said patient.

2. The method of claim 1, wherein said inflammatory condition is selected from the group consisting of intestinal epithelial inflammation, endotoxemia, sepsis, hemorrhagic shock and pancreatitis.

3. The method of claim 2, wherein said intestinal epithelial inflammation is Crohn's disease or ulcerative colitis.

4. The method of claim 1, wherein said composition is administered to said patient enterally.

5. The method of claim 4, wherein said composition is administered using an enteric-coated formulation.

6. The method of claim 1, wherein said composition is administered to said patient systemically.

* * * * *